(12) United States Patent
Dellimore et al.

(10) Patent No.: US 12,383,159 B2
(45) Date of Patent: Aug. 12, 2025

(54) AUTOMATED AND OBJECTIVE SYMPTOM SEVERITY SCORE

(71) Applicant: KONINKLIJKE PHILIPS N.V., Eindhoven (NL)

(72) Inventors: Kiran Hamilton J. Dellimore, Utrecht (NL); Privender Kaur Saini, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 459 days.

(21) Appl. No.: 17/123,913

(22) Filed: Dec. 16, 2020

(65) Prior Publication Data

US 2021/0186370 A1    Jun. 24, 2021

(30) Foreign Application Priority Data

Dec. 19, 2019   (EP) .................................... 19217874

(51) Int. Cl.
*A61B 5/08*    (2006.01)
*A61B 5/00*    (2006.01)

(52) U.S. Cl.
CPC .......... *A61B 5/0816* (2013.01); *A61B 5/0022* (2013.01); *A61B 5/0803* (2013.01); *A61B 5/0823* (2013.01); *A61B 5/741* (2013.01); *A61B 5/7475* (2013.01); *A61B 2562/0219* (2013.01); *A61B 2562/0233* (2013.01)

(58) Field of Classification Search
CPC ... A61B 5/0816; A61B 5/0803; A61B 5/0823; A61B 5/741; A61B 5/7475; A61B 2562/0219; A61B 2562/0233

USPC ........................................................ 600/529
See application file for complete search history.

(56) References Cited

U.S. PATENT DOCUMENTS

| | | |
|---|---|---|
| 10,136,853 B2 | 11/2018 | Heinrich et al. |
| 2005/0235060 A1 | 10/2005 | Brown |
| 2011/0125044 A1 | 5/2011 | Rhee et al. |
| 2014/0114604 A1 | 4/2014 | Zhang et al. |
| 2014/0276228 A1 | 9/2014 | De Waele et al. |
| 2015/0216448 A1 | 8/2015 | Lotan et al. |
| 2018/0035924 A1 | 2/2018 | Gunderson et al. |
| 2018/0206775 A1 | 7/2018 | Saria et al. |

(Continued)

FOREIGN PATENT DOCUMENTS

| | | |
|---|---|---|
| EP | 3200188 A1 | 8/2017 |
| RU | 2571897 C2 | 12/2015 |
| WO | 2018102821 A1 | 6/2018 |

OTHER PUBLICATIONS

Yasin Ozkanca et al., "Depression Screening from Voice Samples of Patients Affected by Parkinson's Disease", Reza Hosseini Ghomi, Department of Neurology, University of Washington, 2019.

(Continued)

*Primary Examiner* — Alex M Valvis
*Assistant Examiner* — Chanel J Jhin
(74) *Attorney, Agent, or Firm* — Michael W. Haas

(57) ABSTRACT

The invention relates to a system and a method for determining a severity of a respiratory disease of a patient. The patient is instructed by a system to recite a phrase. The system receives the phrase recited by the patient as acoustic signal and analyzes the acoustic signal with respect to a severity of a respiratory disease. The result of the analysis is provided, which is indicative for the severity of the respiratory disease of the patient.

6 Claims, 4 Drawing Sheets

(56) References Cited

U.S. PATENT DOCUMENTS

2018/0296092 A1   10/2018  Hassan et al.
2019/0080803 A1    3/2019  Lotan et al.
2019/0200937 A1    7/2019  Mena Benito et al.
2019/0371460 A1* 12/2019  Gutierrez ............ A61M 16/026

OTHER PUBLICATIONS

Mohamed EE, El Maghraby RA. Voice changes in patients with chronic obstructive pulmonary disease. Egyptian Journal of Chest Diseases and Tuberculosis. vol. 63, Issue 3, Jul. 2014, pp. 561-567.

Li Sh et al. Design of Wearable Breathing Sound Monitoring System for Real-Time Wheeze Detection. Sensors 2017, 17, 171.

Ellgring H, Scherer KR. Vocal indicators of mood change in depression. Journal of Nonverbal Behavior, Jun. 1996;20 (2):83-110.

Wang P et al. Automated Video Based Facial Expression Analysis of Neuropsychiatric Disorders. J Neurosci Methods. Feb. 15, 2008; 168(1): 224-238.

Christopher, Alvino CK.; Barrett, Frederick; Gur, Raquel E.; Gur, Ruben C.; Verma, Ragini. Journal of Neuroscience Methods. 2007. Computerized Measurement of Facial Expression of Emotions in Schizophrenia.

* cited by examiner

AUTOMATED AND OBJECTIVE SYMPTOM SEVERITY SCORE

CROSS-REFERENCE TO PRIOR APPLICATIONS

This application claims the benefit of European Patent Application No. 19217874.7, filed on 19 Dec. 2019. This application is hereby incorporated by reference herein.

FIELD OF THE INVENTION

The present invention relates to a system for determining a severity of a respiratory disease of a patient, and a method for determining a severity of a respiratory disease of a patient.

BACKGROUND OF THE INVENTION

Patients who suffer from respiratory diseases like chronic obstructive pulmonary disease often self-manage their condition at home. A daily phone call can be part of the telehealth monitoring of the patients. During this call, patients are typically asked to answer a questionnaire about their symptoms. The responses to these questions can then be used to generate a symptom severity score, which permits the health status of the patient to be evaluated and a risk of exacerbation to be determined. Compliance in answering these questions can often be low, which leads to missing or incomplete data and a calculation of the symptom severity score with a high error probability. In addition, patients may provide inaccurate or unreliable information when responding to the questionnaire, which can further increase the error probability of the symptom severity score.

US2018296092A1 discloses a system and method for monitoring and determining a medical condition of a user, via a communication device of the user. The system comprises a memory and a processor, the processor may be configured to receive an audio signal related to a user's speech, and determine a progress of a disease of the user based on comparing the audio signal to a reference audio signal.

It would be advantageous to have a system and a method for determining a severity of a respiratory disease of a patient that does not suffer from the above-mentioned drawbacks.

SUMMARY OF THE INVENTION

It is an object of the present invention to provide a system and a method for determining a severity of a respiratory disease of a patient with an automated and objective determination of the severity.

The object of the present invention is solved by the subject matter of the independent claims, wherein further embodiments are incorporated in the dependent claims. The described embodiments similarly pertain to the system for determining a severity of a respiratory disease of a patient, and the method for determining a severity of a respiratory disease of a patient. Synergistic effects may arise from different combinations of the embodiments although they might not be described in detail.

Further on, it shall be noted that all embodiments of the present invention concerning a method, might be carried out with the order of the steps as described, nevertheless this has not to be the only and essential order of the steps of the method. The herein presented methods can be carried out with another order of the disclosed steps without departing from the respective method embodiment, unless explicitly mentioned to the contrary hereinafter.

According to a first aspect of the invention, there is provided a system for determining a severity of a respiratory disease of a patient. The system comprises a user interface, wherein the user interface is configured for providing an instruction for reciting a phrase to the patient and wherein the user interface is configured for providing an instruction for performing a physical action to the patient. The system further comprises a receiving device configured for receiving an acoustic signal of the patient, and a measurement unit configured for detecting a movement of the patient. The system further comprises an analyzing device, wherein the analyzing device is configured for analyzing the received acoustic signal with respect to the severity of the respiratory disease, wherein the analyzing device is configured for analyzing the detected movement of the patient with respect to the physical action instructed by the user interface and wherein the analyzing device is configured for providing a result of the analysis of the received acoustic signal, which is indicative for the severity of the respiratory disease of the patient. The analyzing device is configured for determining whether the movement of the patient corresponds to the physical action instructed by the user interface, and the user interface is configured for instructing the patient to recite the phrase in case the detected movement of the patient corresponds to the physical action instructed by the user interface and/or the user interface is configured for repeating the instruction to the patient in case the detected movement of the patient does not correspond to the physical action instructed by the user interface.

The system can determine a severity or a degree of a disease of the patient, which is related to the respiratory system of the patient. Respiratory disease often influence for example the voice or the breathing of the patient and thus can be acoustically detected by analyzing sounds generated by the patient. The system as according to this aspect of the invention comprises an interface, which is used for providing instructions to the patient. This interface can be for example an optic or an acoustic interface, like a screen where the patient can read instructions, or a loudspeaker or headphones providing spoken instructions to the user. These instructions can prompt the patient to recite a phrase, which may be a multi-syllabic sentence. This sentence can comprise several different phonetic sounds, which are suitable to detect the respiratory disease as they are influenced by the respiratory disease. In addition, the sentence may additionally have a positive meaning in order to unconsciously influence the patient. When the phrase is recited by the patient, a receiving device detects the acoustic signal of the patient. The receiving device can be a microphone, which records the voice and related sounds of the patient. An analyzing device analyzes the received acoustic signal with respect to the severity of the respiratory disease. A result of the analysis is provided, which is a measure for the severity or the degree of the respiratory disease of the patient. The severity can be indicated by providing a score, or by providing a trend of the disease. The result can be provided via the interface to the patient. The result can also be stored or transmitted to a care person or a physician. According to the invention, the symptom severity of the patient can be objectively assessed without requiring explicit patient input related to a questionnaire.

The interface can be configured for providing an instruction to the patient for performing a physical action. This action can be a particular movement or a sequence of movements, which can also be performed repeatedly. The number of repetitions can depend on the physical condition of the patient, like age, sex, disease severity or past measurements/checks of the disease severity. The physical action can be suitable to accelerate the breathing of the patient, which may facilitate the analysis of the acoustic signal with respect to the respiratory disease of the patient. The system comprises in this embodiment of the invention a measurement unit, which detects a movement of the patient. The analyzing device is configured for analyzing the detected movement of the patient with respect to the physical action. The analyzing device can compare the detected movement with the physical action and detect whether the movement corresponds to the physical action instructing the user. For comparing the detected movement of the patient with the physical action, a template matching algorithm can be performed. In addition, it may be advantageous to look at the difference of acoustic signals between before and after performing the physical action. Patients with greater disease severity will likely show a greater difference. This may also generally provide additional information on the patient's disease severity.

The analyzing device can compare the detected movement of the patient with the physical action instructed by the user interface. In this embodiment of the invention, the analyzing device can determine whether the patient performs the physical action obediently and correctly.

In case the detected movement corresponds to the physical action and thus the patient follows the instructions, the user interface can instruct the patient to recite the phrase. Otherwise, if the analyzing device cannot detect a movement of the patient corresponding to the physical action, the user interface can repeat the instruction to the patient to perform the physical action. This can be repeated several times. Alternatively, the patient can be informed by the user interface about the importance of performing the physical action, as this is necessary for a correct and reliable result of the analysis of the severity of the respiratory disease of the patient. A chatbot can be provided for communication with the patient. In addition, a care person of the patient or a physician can be informed by the system about the patient not being able or willing to perform the physical action. The chatbot can also be used for data verification, for example to confirm the mood/well-being state of the patient, or by using the chatbot to interact with the patient to acquire more mood/well-being data. Moreover, an interactive chatbot may adapt its interaction with the patient based on the detected mood/well-being state to support the acquisition of additional reliable data. For example, if the patient is in an unhappy mood the chatbot can say motivational phrases to encourage the patient In an embodiment of the invention, the respiratory disease is chronic obstructive pulmonary disease.

The respiratory disease can be chronic obstructive pulmonary disease (COPD). Alternatively, the system according to this embodiment of the invention can be configured for detection other respiratory diseases, like for example asthma.

In an embodiment of the invention, the received acoustic signal of the patient is the voice of the patient, and the analyzing device is configured for analyzing the received acoustic signal with respect to the recited phrase instructed by the user interface.

The received acoustic signal of the patient is in this embodiment of the invention the voice of the patient reciting the phrase. The analyzing device can analyze the acoustic signal and decide whether the patient recited the phrase as instructed by the user interface. Thus, it can be ensured that a reliable and correct analysis of the acoustic signal with respect to the respiratory disease can be performed, as this analysis can be best performed if the patient recites the phrase as instructed. In addition or as an alternative, sounds not directly related to the voice of the patient can be detected and analyzed, like for example breathing or coughing. In addition, words or phrases said by the patient, which are not related to the instructed phrase, can be analyzed by the analyzing device.

In an embodiment of the invention, the analyzing device is configured for analyzing the received acoustic signal of the patient with respect to at least one of: breathing, shortness of breath, wheezing, breathing pitch, frequency of coughs, mood, well-being, voice pitch, flu or infection status, voice timbre, voice amplitude, and combinations thereof, therefrom deriving the severity of the respiratory disease of the patient.

For determining the severity of the respiratory disease of the patient, several parameters can be taking into account by the analyzing device. Which parameter or which combination of parameters is used by the analyzing device to determine the severity of the respiratory disease can depend on the disease to be detected or classified.

In an embodiment of the invention, the analyzing device is configured for analyzing the received acoustic signal with respect to the severity of the respiratory disease based on a comparison of the received acoustic signal with data derived from a plurality of patients.

For determining the severity of the respiratory disease, the received acoustic signal of the patient is in this embodiment of the invention compared with data received from a plurality of patients. The plurality of patients can suffer from the respiratory disease, and they can have different severities of the disease. The diseases of the plurality of patients can be classified by a physician, thereby providing a score of the severity. The severity of the patient can be classified according to a similarity of the received acoustic signal with data of patients with a similar severity. Alternatively, an artificial intelligence module can be used for determining the severity of the disease. The artificial intelligence module can be trained with data sets of a plurality of patients, which comprises acoustic signals of the plurality of the patients with a respective severity score.

In an embodiment of the invention, the system is a communication device, like, for example, a telephone, a smartphone, a tablet, a smart watch, or smart glasses.

The system can be a communication device with an appropriate application installed on it. The screen or the speakers can be used as user interface, whereas the microphone can be used as receiving device for receiving the acoustic signal of the patient. An inertial measurement unit of the communication device can be used as measurement unit for detecting the movement of the patient and the analyzing device can be the processor of the communication device. The communication device can establish a connection via a data connection or a voice connection to instruct the patient via the internet or via a telephone call. The received acoustic signal and/or the measured movement can be transmitted via the connection and can be analyzed by a server as analyzing device.

In an embodiment of the invention, the measurement unit comprises an inertial measurement unit comprising an accelerometer, a gyroscope, and/or a barometric sensor.

The measurement unit is configured for detecting a movement of the patient. This can be achieved by an inertial measurement unit. The inertial measurement unit can comprise one or more accelerometers and or a gyroscope. Also a barometric sensor can be used to detect a movement of the patient, as relative changes of the height of the barometric sensor and therefore the patient can be determined.

In an embodiment of the invention, the measurement unit comprises a camera.

A camera can record a video or a sequence of images of the patient. By analyzing this video or the images of the camera, a movement of the patient can be determined. The camera may be used in addition to the inertial measurement unit to increase the reliability of detecting incorrect or false movement of the patient in situations in which the signal of the inertial measurement unit is artifacted, for example, due to coughing or talking during the movement, or environmental noise. Furthermore, the data from the camera may be processed to provide additional objective parameters about the patient's current health status. In particular, the video data may be processed to confirm the patient's mood/well-being status to improve the assessment based only on voice pitch. Assessment of mood/well-being status from imaging data can be performed using facial expression classifiers, such as the Nearest Neighbor classifier, Neural Networks, SVM, Bayesian Networks, AdaBoost classifier, and multi-level Hidden Markov Models.

In an embodiment of the invention, the physical action instructed by the user interface can be a sit-to-stand test, a forced expiratory maneuver, a timed get up and go movement, and/or a Valsalva maneuver. The "sit-to-stand test" is a widely used assessment tool that measures lower body strength, balance, and mobility. During this test, the participant sits in a chair with their feet flat on the floor and arms crossed over your chest. They are required to stand up completely without using your hands or arms for assistance. They then sit back down and repeat the process as many times as possible within 30 seconds. The "timed get up and go TUG)" movement is an assessment tool test assesses mobility, balance, and fall risk by measuring the time it takes a person to rise from a chair, walk 3 meters, turn, walk back, and sit down.

The physical action to be performed by the patient can be an action, which stresses the patient and increases the heart rate and the breathing frequency, like for example a sit-to-stand test or a get up and go movement. Alternatively or in addition, the physical action can be a movement or a maneuver of the patient's respiratory system like a forced expiratory maneuver or a Valsalva maneuver.

According to another aspect of the invention, there is provided a method for determining a physical condition of a patient. The method comprises the steps of providing an instruction for reciting a phrase to the patient, receiving an acoustic signal of the patient, analyzing the received acoustic signal with respect to the severity of the respiratory disease, and providing a result of the analysis of the received acoustic signal, which is indicative for the physical condition of the patient.

The method according to the invention determines a physical condition of a patient. In a first step, an instruction for reciting a phrase is provided to the patient. In a second step, an acoustic signal of the patient is received, which can be the voice of the patient and/or other sounds created by the patient. In a third step, the received acoustic signal is analyzed with respect to the severity of the respiratory disease of the patient. In a fourth step, a result of the analysis of the received acoustic signal is provided, which is indicative for the physical condition of the patient.

The method further comprises the steps of providing an instruction for performing a physical action to the patient, detecting a movement of the patient, and analyzing the detected movement of the patient with respect to the physical action.

The method further comprises steps of providing an instruction for performing a physical action to the patient and detecting a movement of the patient, which is followed by the steps of analyzing the detected movement of the patient with respect to the physical action, determining whether the movement of the patient corresponds to the physical action, repeating the instruction to the patient in case the detected movement of the patient does not correspond to the physical action, providing an instruction for reciting a phrase to the patient in case the detected movement of the patient corresponds to the physical action. These steps are preferably performed before the first step of providing an instruction for reciting a phrase to the patient is performed. Thus, it can be assured that the patient is only instructed to recite the phrase after having performed the physical action. In addition, it may be advantageous to look at the difference of acoustic signals between before and after performing the physical action. Patients with worse physical condition will likely show a greater difference. This may also generally provide additional information on the patient's physical condition.

The method is in this embodiment of the invention automatically performed by a system for determining a severity of a respiratory disease of a patient. The method can be performed by a communication device like a smartphone with or without network connection. There is no need for a human operator like a physician to perform any steps of the method.

According to another aspect of the invention, there is provided a computer program element, which, when executed on a processing unit, instructs the processing unit to perform the method according to any of the preceding embodiments.

The computer program element can be performed on one or more processing units, which are instructed to perform the method for determining a physical condition of a patient.

According to another aspect of the invention, there is provided a processing unit configured for executing the computer program element according to the preceding embodiment.

The processing unit can be, for example, a processor of a communication device like a telephone, a smartphone, a tablet, a smart watch or smart glasses. The processing unit can also be distributed over one or more different devices, such that a part of the computer program element can be executed on the communication device, and another part for example on a server.

Thus, the benefits provided by any of the above aspects equally apply to all of the other aspects and vice versa.

In a gist, the invention relates to a system and a method for determining a severity of a respiratory disease of a patient. The patient is instructed by a system to recite a phrase. The system receives the phrase recited by the patient as acoustic signal and analyzes the acoustic signal with respect to a severity of a respiratory disease. The result of the analysis is provided, which is indicative for the severity of the respiratory disease of the patient.

The above aspects and embodiments will become apparent from and be elucidated with reference to the exemplary embodiments described hereinafter. Exemplary embodiments of the invention will be described in the following with reference to the following drawings:

DETAILED DESCRIPTION OF EMBODIMENTS

Figure 1:
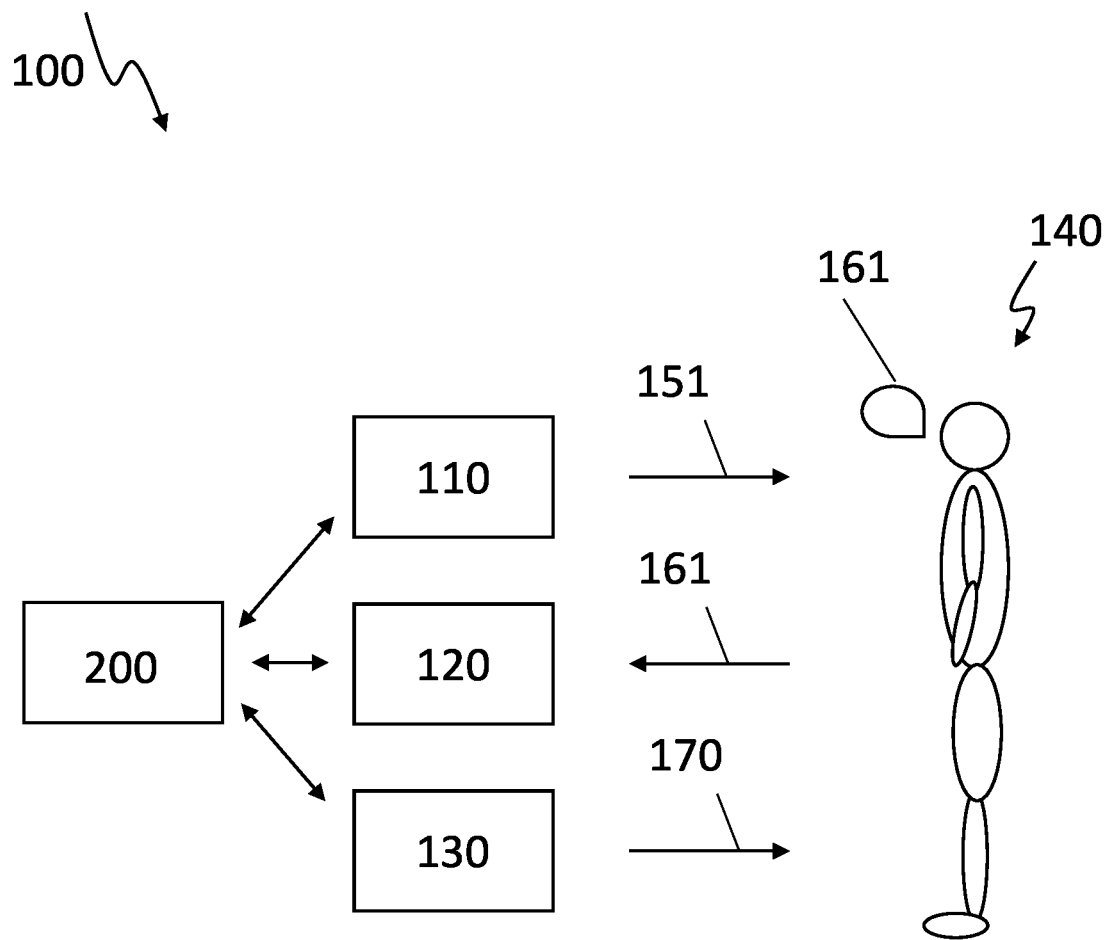
FIG. 1 shows a schematic set-up of a system for determining a severity of a respiratory disease of a patient according to a first embodiment of the invention.

FIG. 1 shows a schematic set-up of a system 100 for determining a severity of a respiratory disease of a patient 140 according to a first embodiment of the invention. A user interface 110 instructs the patient 140 to recite a phrase 151. An acoustic signal 161 of the patient 140, which can be the voice of the patient 140 reciting the phrase 151 is received by the receiving device 120. An analyzing device 130 analyzes the acoustic signal with respect to a respiratory disease of the patient. A result 170 of the analysis is provided. The result 170 can be provided to the patient 140 and/or to a care person or physician of the patient 140. A processing unit 200 can be communicationally connected to the user interface 110, the receiving device 120 and the analyzing device 130.

Figure 2:
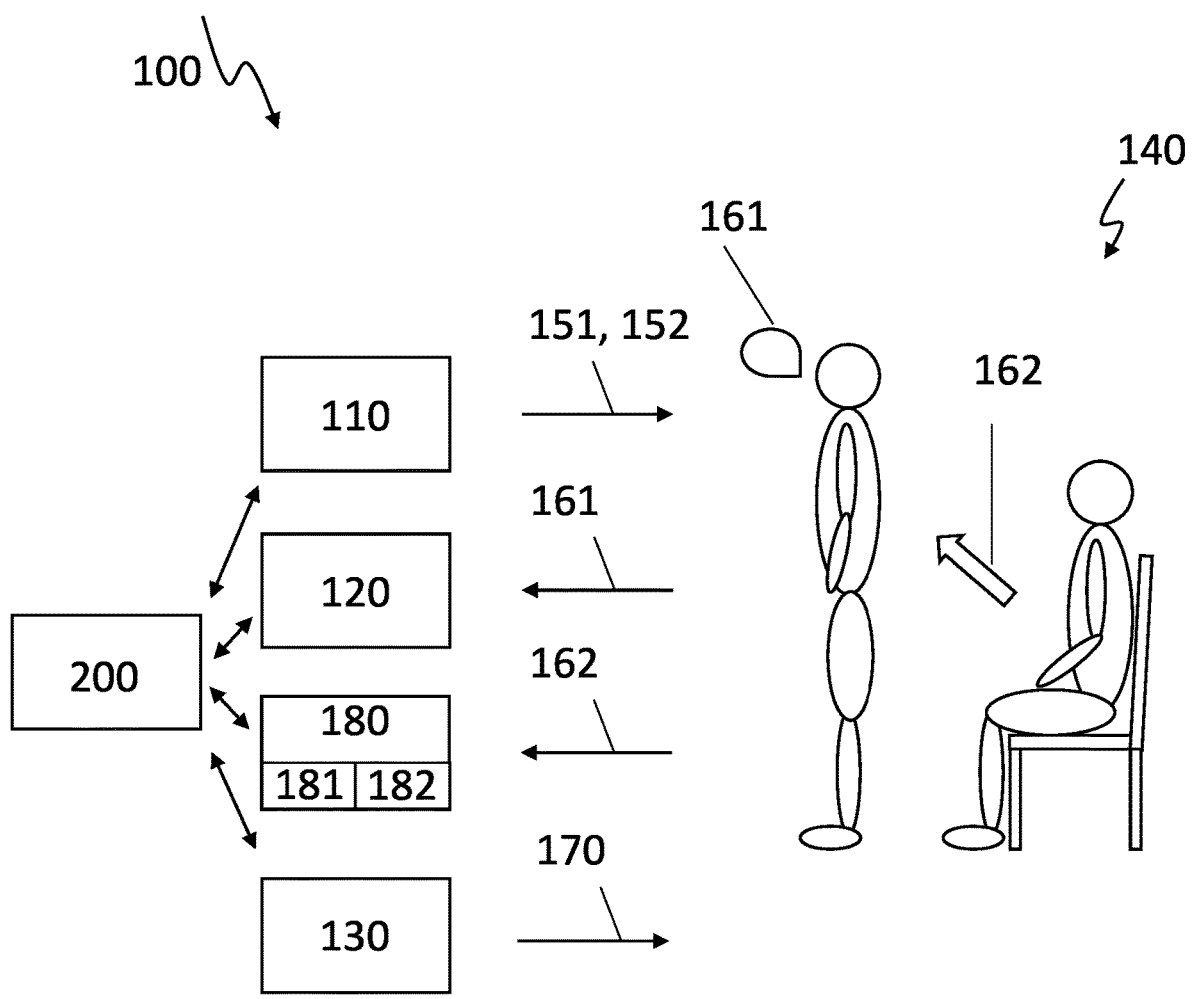
FIG. 2 shows a schematic set-up of a system for determining a severity of a respiratory disease of a patient according to a second embodiment of the invention.

FIG. 2 shows a schematic set-up of a system 100 for determining a severity of a respiratory disease of a patient 140 according to a second embodiment of the invention. The user interface 110 is configured to provide an instruction to the patient 140 to perform a physical action 152, and to provide an instruction to the patient to recite a phrase 151. The patient 140 can perform a movement 162, which can correspond to the physical action 152. A measurement unit 180 is configured for detecting the movement 162 of the patient 140. The measurement unit 180 can comprise an inertial measurement unit 181 and/or a camera 182. An acoustic signal 161 of the patient 140, which can be the voice of the patient 140 reciting the phrase 151 is received by the receiving device 120. The analyzing device 130 analyses the detected movement 162 with respect to the instructed physical action 152. The analyzing device 130 analyses the acoustic signal 161 with respect to a respiratory disease of the patient 140. The analysis of the acoustic signal 161 may only be performed in case the detected movement 162 corresponds to the instructed physical action 152. A result 170 of the analysis is provided. The result can be provided to the patient 140 and/or to a care person or physician of the patient 140. A processing unit 200 can be communicationally connected to the user interface 110, the receiving device 120, the measurement unit 180, and the analyzing device 130.

Figure 3:
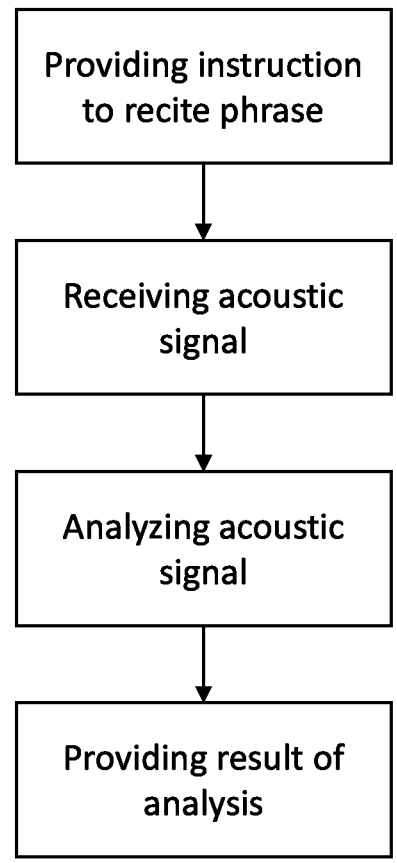
FIG. 3 shows a block diagram of a method for determining a severity of a respiratory disease of a patient.

FIG. 3 shows a block diagram of a method for determining a severity of a respiratory disease of a patient 140. The method comprises a first step of providing an instruction for reciting a phrase 151 to the patient 140. This step is followed by the second step of receiving an acoustic signal 161 of the patient 140. The third step comprises analyzing the received acoustic signal 161 with respect to the severity of the respiratory disease. The fourth step comprises providing a result of the analysis of the received acoustic signal 161, which is indicative for the severity of the respiratory disease of the patient 140.

Figure 4:
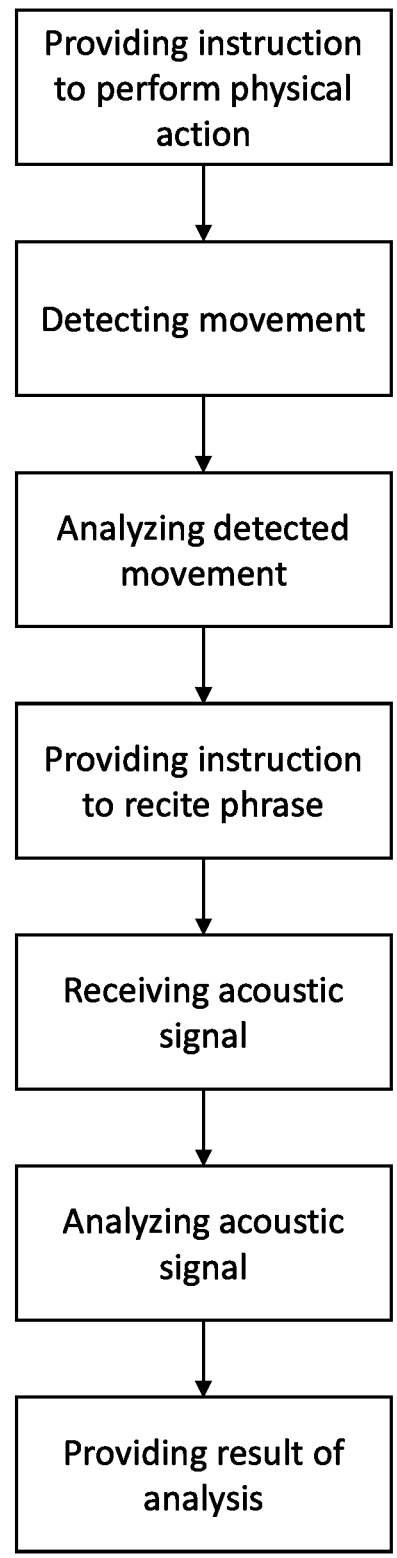
FIG. 4 shows a block diagram of a method for determining a severity of a respiratory disease of a patient according to an embodiment of the invention.

FIG. 4 shows a block diagram of a method for determining a severity of a respiratory disease of a patient 140 according to an embodiment of the invention. This embodiment of the invention comprises compared to the method shown in FIG. 3 three additional steps, which can be preferably performed before the first step. However, also a different order of the steps can be possible. These three additional steps are providing an instruction for performing a physical action 152 to the patient 140, detecting a movement 162 of the patient 140, and analyzing the detected movement 162 of the patient 140 with respect to the physical action 152.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. The mere fact that certain measures are re-cited in mutually different dependent claims does not indicate that a combination of these measures cannot be used to advantage. Any reference signs in the claims should not be construed as limiting the scope.

The invention claimed is:

1. A system for determining a severity of a specific respiratory disease of a patient, the system comprising:
   a user interface;
   an acoustic receiving device;
   a movement measurement unit;
   an analyzing device; and
   a processing unit configured to: (i) cause the user interface to provide a first instruction to the patient for performing a physical action which requires the patient to move in a specified manner, (ii) cause the analyzing device to analyze movement of the patient detected by the movement measurement unit after and in response to the first instruction and determine whether the detected movement of the patient corresponds to the physical action, (iii) responsive to determining that the detected movement of the patient corresponds to the physical action, cause the user interface to provide a second instruction to the patient for reciting a phrase, (iv) cause the analyzing device to analyze an acoustic signal received by the acoustic receiving device after and in response to the second instruction by comparing the received acoustic signal to a plurality of other acoustic signals received from a plurality of other patients, wherein each of the other patients suffers from the specific respiratory disease with a specific disease severity and wherein the specific disease severity of at least some of the plurality of other patients is different than the specific disease severity of others of the plurality of other patients, wherein each of the other acoustic signals has been classified by a physician and each of the other patients has been assigned an associated severity score determined by the physician, wherein the comparing includes determining a similarity of the received acoustic signal to each of the other acoustic signals, (v) cause the analyzing device to classify the severity of the specific respiratory disease of the patient and assign a severity score to the patient based on each of the determined similarities and each of the assigned associated severity scores of the plurality of other patients, and (vi) provide an output from the system on the user interface including the severity score assigned to the patient, and wherein the physical action instructed by the user interface is one or more of a sit-to-stand test or a timed get up and go movement.

2. The system according to claim 1, wherein the respiratory disease is chronic obstructive pulmonary disease.

3. The system according to claim 1, wherein the received acoustic signal of the patient is the voice of the patient, and wherein the analyzing device is configured for analyzing the received acoustic signal with respect to the recited phrase instructed by the user interface.

4. The system according to claim 1, wherein the system is a communication device comprising a telephone, a smartphone, a tablet, a smart watch, or smart glasses.

5. The system according to claim 1, wherein the movement measurement unit comprises: (i) an inertial measurement unit comprising one or more of an accelerometer, a gyroscope, for a barometric sensor, or (ii) a camera.

6. A system for determining a severity of a specific respiratory disease of a patient, the system comprising: a user interface; an acoustic receiving device; a movement measurement unit; an analyzing device implementing a trained artificial intelligence model; and a processing unit configured to: (i) cause the user interface to provide a first instruction to the patient for performing a physical action which requires the patient to move in a specified manner, (ii) cause the analyzing device to analyze movement of the patient detected by the movement measurement unit after and in response to the first instruction and determine whether the detected movement of the patient corresponds to the physical action, (iii) responsive to determining that the detected movement of the patient corresponds to the physical action, cause the user interface to provide a second instruction to the patient for reciting a phrase, (iv) cause the analyzing device to analyze an acoustic signal received by the acoustic receiving device after and in response to the second instruction by providing the received acoustic signal to the trained artificial intelligence model, wherein the trained artificial intelligence model is trained with a plurality of other acoustic signals received from a plurality of other patients each suffering from the specific respiratory disease, wherein each of the other acoustic signals has been classified by a physician and each of the other acoustic signals has been assigned an associated severity score determined by the physician, and wherein the trained artificial intelligence model is configured to determine a severity score of the specific respiratory disease of the patient based on the received acoustic signal, and (v) provide an output from the system on the user interface including the severity score determined for the patient, and wherein the physical action instructed by the user interface is one or more of a sit-to-stand test or a timed get up and go movement.

* * * * *